United States Patent
Wright et al.

(10) Patent No.: US 8,946,292 B2
(45) Date of Patent: Feb. 3, 2015

(54) FORMULATIONS OF LOW DOSE DICLOFENAC AND BETA-CYCLODEXTRIN

(75) Inventors: Curtis Wright, Rockport, MA (US); Daniel B. Carr, Chestnut Hill, MA (US); Fred H. Mermelstein, Newtown, MA (US)

(73) Assignee: Javelin Pharmaceuticals, Inc., Lake Forest, IL (US)

( * ) Notice: Subject to any disclaimer, the term of this patent is extended or adjusted under 35 U.S.C. 154(b) by 0 days.

(21) Appl. No.: 13/106,697

(22) Filed: May 12, 2011

(65) Prior Publication Data

US 2011/0218247 A1    Sep. 8, 2011

Related U.S. Application Data

(63) Continuation of application No. 11/689,931, filed on Mar. 22, 2007, now Pat. No. 8,580,954.

(60) Provisional application No. 60/786,486, filed on Mar. 28, 2006.

(51) Int. Cl.
| | |
|---|---|
| A61K 31/196 | (2006.01) |
| A61K 31/195 | (2006.01) |
| A61K 31/724 | (2006.01) |
| C07H 3/06 | (2006.01) |
| C07H 15/04 | (2006.01) |
| C08B 37/16 | (2006.01) |
| A61K 47/40 | (2006.01) |

(52) U.S. Cl.
CPC ............. *A61K 31/196* (2013.01); *A61K 31/195* (2013.01); *A61K 31/724* (2013.01); *C07H 3/06* (2013.01); *C07H 15/04* (2013.01); *C08B 37/0015* (2013.01); *A61K 47/40* (2013.01)
USPC .......................................... 514/567; 562/496

(58) Field of Classification Search
None
See application file for complete search history.

(56) References Cited

U.S. PATENT DOCUMENTS

| | | | |
|---|---|---|---|
| 4,711,906 A | 12/1987 | von Stetten et al. |
| 4,727,064 A | 2/1988 | Pitha |
| 4,764,604 A | 8/1988 | Muller |
| 4,983,586 A | 1/1991 | Bodor |
| 5,017,566 A | 5/1991 | Bodor |
| 5,024,998 A | 6/1991 | Bodor |
| 5,354,560 A | 10/1994 | Lovrecich |
| 5,389,681 A | 2/1995 | Galli |
| 5,449,521 A | 9/1995 | Lovrecich |
| 5,464,633 A | 11/1995 | Conte et al. |
| 5,674,854 A | 10/1997 | Bodley et al. |
| 5,679,660 A | 10/1997 | Bodley et al. |
| 5,681,583 A | 10/1997 | Conte et al. |
| 5,690,954 A | 11/1997 | Illum |
| 5,702,724 A | 12/1997 | Stahl et al. |
| 5,738,874 A | 4/1998 | Conte et al. |
| 5,747,058 A | 5/1998 | Tipton et al. |
| 5,747,061 A | 5/1998 | Amselem et al. |
| 5,785,989 A | 7/1998 | Stanley et al. |
| 5,811,547 A | 9/1998 | Nakamichi et al. |
| 5,821,237 A | 10/1998 | Bissett et al. |
| 5,854,226 A | 12/1998 | Penkler et al. |
| 5,866,162 A | 2/1999 | Grattan |
| 5,891,913 A | 4/1999 | Sallmann et al. |
| 5,929,115 A | 7/1999 | Takeuchi et al. |
| 6,028,222 A | 2/2000 | Dietlin et al. |
| 6,071,964 A | 6/2000 | Fischer et al. |
| 6,107,343 A | 8/2000 | Sallmann et al. |
| 6,294,192 B1 | 9/2001 | Patel et al. |
| 6,365,180 B1 | 4/2002 | Meyer et al. |
| 6,407,079 B1 | 6/2002 | Müller et al. |
| 6,828,299 B2 | 12/2004 | Yang et al. |
| 6,869,939 B2 | 3/2005 | Mosher et al. |
| 6,923,988 B2 | 8/2005 | Patel et al. |
| 7,115,586 B2 | 10/2006 | Loftsson |
| 7,186,260 B2 | 3/2007 | Hyson |
| 7,423,028 B2 | 9/2008 | Zoppetti et al. |
| 7,655,231 B2 | 2/2010 | Shelton et al. |
| 2002/0012680 A1 | 1/2002 | Patel et al. |
| 2002/0034539 A1 | 3/2002 | Esposito et al. |
| 2002/0035264 A1 | 3/2002 | Kararli et al. |
| 2002/0107265 A1 | 8/2002 | Chen et al. |
| 2003/0082234 A1 | 5/2003 | Seo et al. |
| 2003/0113367 A1 | 6/2003 | Penkler |

(Continued)

FOREIGN PATENT DOCUMENTS

| | | |
|---|---|---|
| DE | 4207922 | 9/1993 |
| DE | 69820973 T2 | 12/2004 |

(Continued)

OTHER PUBLICATIONS

Nagarsenker et al., "Solid dispersion of hydroxyproply beta-cyclodextrin and ketrolac: enhancement of in-vitro dissolution rates, improvement in anti-inflammatory activity and reduction in ulcerogenicity in rats", *Journal of Pharmacy and Pharmacology*, 52(8):949-956, Aug. 2000.

(Continued)

*Primary Examiner* — Eric Olson
(74) *Attorney, Agent, or Firm* — Baker Botts LLP (57) ABSTRACT

The present invention is directed to a pharmaceutical composition containing a unit dose of a diclofenac compound effective to induce analgesia; and a beta-cyclodextrin compound; wherein the dose of the diclofenac compound is less than 75 mg, e.g., from about 18.75 mg to about 37.5 mg. The present invention is also directed to methods of treating a subject in need of analgesia with the pharmaceutical compositions of the invention.

5 Claims, 2 Drawing Sheets

(56) References Cited

U.S. PATENT DOCUMENTS

| | | |
|---|---|---|
| 2003/0139698 A1 | 7/2003 | Hyson |
| 2003/0232089 A1 | 12/2003 | Singh et al. |
| 2004/0024044 A1 | 2/2004 | Di Salle et al. |
| 2004/0072798 A1 | 4/2004 | Naggi et al. |
| 2004/0137062 A1 | 7/2004 | Chopra |
| 2004/0151774 A1 | 8/2004 | Pauletti et al. |
| 2004/0157796 A1 | 8/2004 | Gokarn |
| 2005/0043481 A1 | 2/2005 | Gref et al. |
| 2005/0085446 A1 | 4/2005 | Babu et al. |
| 2005/0095205 A1 | 5/2005 | Krishnamoorthy |
| 2005/0118272 A1 | 6/2005 | Besse et al. |
| 2005/0197303 A1 | 9/2005 | Krishnamoorthy |
| 2005/0203115 A1 | 9/2005 | Sancilio et al. |
| 2005/0238674 A1 | 10/2005 | Penkler et al. |
| 2005/0276841 A1 | 12/2005 | Davis et al. |
| 2006/0024238 A1 | 2/2006 | Barth et al. |
| 2006/0121085 A1 | 6/2006 | Warren et al. |
| 2006/0134095 A1 | 6/2006 | Ito et al. |
| 2006/0188530 A1 | 8/2006 | Yoo |
| 2006/0210604 A1 | 9/2006 | Dadey et al. |
| 2006/0211599 A1 | 9/2006 | Suzuki |
| 2007/0049552 A1 | 3/2007 | Babu et al. |
| 2007/0116730 A1 | 5/2007 | Simmons |
| 2007/0207222 A1 | 9/2007 | Yu |
| 2007/0219170 A1 | 9/2007 | Samson |
| 2007/0232566 A1 | 10/2007 | Wright et al. |
| 2007/0232567 A1 | 10/2007 | Wright et al. |
| 2008/0171014 A1 | 7/2008 | Wu et al. |
| 2008/0200533 A1 | 8/2008 | Krishnan |
| 2008/0220441 A1 | 9/2008 | Birnbaum et al. |
| 2009/0292022 A1 | 11/2009 | Kowalski et al. |
| 2012/0142779 A1 | 6/2012 | Penkler et al. |

FOREIGN PATENT DOCUMENTS

| | | |
|---|---|---|
| DE | 69434356 T2 | 5/2006 |
| EP | 0268215 | 5/1988 |
| EP | 0335545 | 10/1989 |
| EP | 0371431 | 6/1990 |
| EP | 446753 A1 | 9/1991 |
| EP | 0519428 | 12/1992 |
| EP | 598337 | 5/1994 |
| EP | 0647451 | 4/1995 |
| EP | 0658347 | 6/1995 |
| EP | 807434 | 11/1997 |
| EP | 868915 | 10/1998 |
| EP | 1004318 | 5/2000 |
| EP | 862414 | 12/2001 |
| EP | 833618 | 4/2002 |
| EP | 730443 | 5/2002 |
| EP | 1219304 | 7/2002 |
| EP | 1219306 | 7/2002 |
| EP | 729748 | 2/2003 |
| EP | 0658347 | 8/2003 |
| EP | 0701449 | 8/2003 |
| EP | 917457 | 1/2004 |
| EP | 792147 | 3/2004 |
| EP | 1574221 | 9/2005 |
| EP | 1595936 | 11/2005 |
| EP | 1609481 | 12/2005 |
| EP | 1681065 | 7/2006 |
| EP | 1767219 | 3/2007 |
| EP | 1524968 | 12/2007 |
| EP | 1515729 | 2/2008 |
| EP | 1677761 | 4/2008 |
| EP | 1967186 | 9/2008 |
| EP | 1974751 | 10/2008 |
| GB | 2 230 440 | 10/1990 |
| GB | 2417900 A | 3/2006 |
| JP | 59-084821 | 5/1984 |
| JP | 62138437 | 6/1987 |
| JP | 1-287094 | 11/1989 |
| JP | 06-16547 | 1/1994 |
| JP | 7196484 | 8/1995 |
| JP | 7252144 | 10/1995 |
| JP | 9-48737 | 2/1997 |
| JP | 2006-502185 | 1/2006 |
| WO | WO9002141 | 3/1990 |
| WO | WO9200725 | 1/1992 |
| WO | WO9203122 | 3/1992 |
| WO | WO9406416 | 3/1994 |
| WO | WO9428936 | 12/1994 |
| WO | WO9501781 | 1/1995 |
| WO | WO9504528 | 2/1995 |
| WO | WO9507104 | 3/1995 |
| WO | WO9511669 | 5/1995 |
| WO | WO9532737 | 12/1995 |
| WO | WO9611003 | 4/1996 |
| WO | WO9614839 | 5/1996 |
| WO | WO9622088 | 7/1996 |
| WO | WO 96/41646 | 12/1996 |
| WO | WO9641617 | 12/1996 |
| WO | WO9710805 | 3/1997 |
| WO | WO9735568 | 10/1997 |
| WO | WO9851280 | 11/1998 |
| WO | WO9936060 | 7/1999 |
| WO | WO0050007 | 8/2000 |
| WO | WO0059475 | 10/2000 |
| WO | WO 00/66099 | 11/2000 |
| WO | WO0071098 | 11/2000 |
| WO | WO0113897 | 3/2001 |
| WO | WO0128555 | 4/2001 |
| WO | WO 01/41760 | 6/2001 |
| WO | WO0145742 | 6/2001 |
| WO | WO0180797 | 11/2001 |
| WO | WO0205815 | 1/2002 |
| WO | WO0220020 | 3/2002 |
| WO | WO02053188 | 7/2002 |
| WO | WO02072106 | 9/2002 |
| WO | WO 03/018009 | 3/2003 |
| WO | WO03033025 | 4/2003 |
| WO | WO 03/063824 | 8/2003 |
| WO | WO 03/095498 | 11/2003 |
| WO | WO03097011 | 11/2003 |
| WO | WO03105867 | 12/2003 |
| WO | WO2004041118 | 5/2004 |
| WO | WO2004081196 | 9/2004 |
| WO | WO2004089418 | 10/2004 |
| WO | WO2005044231 | 5/2005 |
| WO | WO2005074887 | 8/2005 |
| WO | WO2005077336 | 8/2005 |
| WO | WO2005086763 | 9/2005 |
| WO | WO2005092387 | 10/2005 |
| WO | WO2005120578 | 12/2005 |
| WO | WO2005123193 | 12/2005 |
| WO | WO2006007753 | 1/2006 |
| WO | WO2006041942 | 4/2006 |
| WO | WO2006082588 | 8/2006 |
| WO | WO2007004236 | 1/2007 |
| WO | WO2007005608 | 1/2007 |
| WO | WO2007044062 | 4/2007 |
| WO | WO2007052289 | 5/2007 |
| WO | WO2007059591 | 5/2007 |
| WO | WO2007061828 | 5/2007 |
| WO | WO2007103435 | 9/2007 |
| WO | WO2007103687 | 9/2007 |
| WO | WO2007106381 | 9/2007 |
| WO | WO2007112272 | 10/2007 |
| WO | WO2007112274 | 10/2007 |
| WO | WO2008006216 | 1/2008 |
| WO | WO2008040534 | 4/2008 |
| WO | WO2008071851 | 6/2008 |
| WO | WO2008074087 | 6/2008 |
| WO | WO2008076703 | 6/2008 |
| WO | WO2008115572 | 9/2008 |
| WO | WO2008127271 | 10/2008 |
| WO | WO2008127291 | 10/2008 |
| WO | WO2008133982 | 11/2008 |
| WO | WO2008134600 | 11/2008 |
| WO | WO2008134601 | 11/2008 |

OTHER PUBLICATIONS

U.S. Appl. No. 11/689,931, filed Mar. 22, 2007.

(56) References Cited

OTHER PUBLICATIONS

U.S. Appl. No. 11/689,939, filed Mar. 22, 2007.
U.S. Appl. No. 11/689,931, Apr. 6, 2011 Non-Final Office Action.
U.S. Appl. No. 11/689,931, Feb. 10, 2011 Respone to Non-Final Office Action.
U.S. Appl. No. 11/689,931, Nov. 10, 2011 Non-Final Office Action.
U.S. Appl. No. 11/689,931, Sep. 9, 2010 Response to Non-Final Office Action.
U.S. Appl. No. 11/689,931, Mar. 10, 2010 Non-Final Office Action.
U.S. Appl. No. 11/689,931, Oct. 16, 2009 Amendment and Request for Continued Examination (RCE).
U.S. Appl. No. 11/689,931, Apr. 17, 2009 Final Office Action.
U.S. Appl. No. 11/689,931, Jan. 7, 2009 Response to Non-Final Office Action.
U.S. Appl. No. 11/689,931, Sep. 25, 2008 Non-Final Office Action.
U.S. Appl. No. 11/689,939, Apr. 1, 2011 Final Office Action.
U.S. Appl. No. 11/689,939, Feb. 10, 2011 Response to Non-Final Office Action.
U.S. Appl. No. 11/689,939, Sep. 10, 2011 Non-Final Office Action.
U.S. Appl. No. 11/689,939, Jul. 1, 2010 Examiner's Interview Summary.
U.S. Appl. No. 11/689,939, Jun. 23, 2010 Response to Non-Final Office Action.
U.S. Appl. No. 11/689,939, Dec. 31, 2009 Non-Final Office Action.
U.S. Appl. No. 11/689,939, Oct. 28, 2009 Amendment and Request for Examination (RCE).
U.S. Appl. No. 11/689,939, Apr. 29, 2009 Final Office Action.
U.S. Appl. No. 11/689,939, Jan. 7, 2009 Response to Non-Final Office Action.
U.S. Appl. No. 11/689,939, Sep. 19, 2008 Non-Final Office Action.
Adis Drugs Monograph on Diclofenac (2008).
Anderson et al., "Diclofenac in Combination With Opiate Infusion After Joint Replacement Surgery", Anaesth. Intens. Care, (1991), 19:535-538.
Backensfeld et al., "Interaction of NSA with Cyclodextrins and Hydroxypropyl Cyclodextrin Derivatives", Int. J. Pharm., (1991), 74:85-93.
Backensfeld et al., "Solubilization and Stabilization of Non-Steroidal Antirheumatics with Cyclodextrins and Cyclodextrin Ethers", Arch. Pharm., (1990), 323:690.
Barbato F. et al. "Diclofenac beta-Cyclodextrin Binary Systems: A Study in Solution and in the Solid State," J. Inclusion Phenomena and Macrocyclic Chem. vol. 46, Aug. 2003, pp. 179-185.
Blaicher et al., "Effect of non-selective, non-steroidal anti-inflammatory drugs and cyclo-oxygenase-2 selective inhibitors on the PFA-100 closure time", Anaesthesia, (2004), 59:1100-1103.
Bricker et al., "Peri-operative blood loss and non-steriodal anti-inflammatory drugs: an investigation using diclofenac in patients undergoing transurethral resection of the prostate", European Journal of Anaesthesiology, (1987), 4:429-434.
Brogden et al., *Drugs* 20(1): 24-48 (1980).
Campbell et al., "Intravenous diclofenac sodium", Anaethesia, (1990), 45:763-766.
Coakley et al., "Use of the platelet function analyser (PFA-100®) to quantify the effect of low dose aspirin in patients with ischaemic heart disease", Anaesthesia, (2005), 60:1173-1178.
Dahl et al., "High-dose diclofenac for postoperative analgesia after elective caesarean section in regional anaesthesia", Int. J. Obstet. Anesth., (2002), 11(2):91-94.
Devi et al., "Albumin Microspheres and beta-Cyclodextrin Inclusion Complex Containing Diclofenac Sodium", Ind. J. Pharm. Sci, (1992), 54:259-261.
Ejnell et al., "Treatment of postoperative pain with diclofenac in uvulopalatopharyngoplasty", British Journal of Anaesthesia, (1992), 68:76-80.
European Search Report for EP Patent Application No. 07759156.
European Search Report (Appln No. 04257437.6-1219, dated Jun. 15, 2005).
FDA label for BEXTRA® valdecoxib tablets, revised Nov. 2004, downloaded from www.fda.gov.
FDA product label for diclofenac, http://www.drugs.com/pro/diclofenac.html.
Final Study Report, Randomized, double-blind, placebo and comparator controlled, single-dose, parallel-group comparison of the analgesic efficacy and safety of intravenous DIC075V (diclofenac sodium) injection, ketorolac tromethamine, and placebo following study (Jun. 4, 2009).
Graham, "COX-2 Inhibitors, Other NSAIDs, and Cardiovascular Risk", JAMA, (2006), 296.
Gunnison et al., "Sulfite Hypersensitivity, a Critical Review", CRC Critical Reviews in Toxicology, (1987), 17(3):185-214.
Hawley's Condensed Chemical Dictionary, 1997, p. 603.
Heaney et al., "Sequential clot strength analyses following diclofenac in pediatric adenotonsillectomy", Pediatric Anethesia, (2007), 17:1078-1082.
Hegi et al., "Effect of rofecoxib on platelet aggregation and blood loss in gynaecological and breast surgery compared with diclofenac", British Journal of Anaesthesia, (2004), 92(4):523-531.
Hersh et al, *Clin. Ther.* 26(8):1215-27 (2004).
Hyrkäs, "Effect of Preoperative Single Doses of Diclofenac and Methylprednisolone on Wound Healing", Scand. J. Plast. Reconstr. Hand Surg., (1994), 28:275-278.
Ikeda et al., "Inclusion Complexes of beta-Cyclodextrin with Antiinflammatory Drugs Fenamates in Aqueous Solution", Chem. Pharm. Bull., (1975), 23(1):201-208.
Jambhekar et al., "The physicochemical characteristics and bioavailability of indomethacin from beta-cyclodextrin, hydroxyethyl-beta-cyclodextrin, and hydroxypropyl-beta-cyclodextrin complexes", (2004), Int. J. Pharm., 270(1-2):149-66.
Kasrarian et al., "Developing an injectable formula containing an oxygen-sensitive drug: a case study of danofloxacin injectable" Pharm. Dev. Technol., (1999), 4(4):475-80.
Kokki, "Nonsteroidal anti-inflammatory drugs for postoperative pain: a focus on children", Paediatr. Drugs, (2003), 5(2):103-123.
Kundu et al., "Description of an in Vitro Platelet Function Analyzer—PFA-100™", Seminars in Thrombosis and Hemostasis, (1995), 21(2):106-112.
Kurozumi et al., "Inclusion Compounds of Non-Steroidal Antiinflammatory and Other Slightly Water Soluble Drugs with alpha-and beta-Cyclodextrins in Powdered Form," Chem. Pharm. Bull., (1975), 23:3062-3068.
Laitinen et al., "Intravenous Diclofenac Coupled with PCA Fentanyl for Pain Relief after Total Hip Replacement", Anesthesiology, (1992), 76:194-198.
Laitinen et al., "Effect of a non-steriodal anti-inflammatory drug, diclofenac, on haemostasis in patients undergoing total hip replacement", Acta. Anaesthesiol. Scand., (1992), 36:486-489.
Leese et al., "Valdecoxib Does Not Impair Platelet Function", American Journal of Emergency Medicine, (2002), 20(4):275-281.
Legeby et al., "Analgesic efficacy of diclofenac in combination with morphine and paracetamol after mastectomy and immediate breast reconstruction", Acta. Anaethesiol. Scand., (2005), 49:1360-1366.
Lewis et al., "Dose-response relationships between individual nonaspirin nonsteroidal anti-inflammatory drugs (NANSAIDs) and serious upper gastrointestinal bleeding: a meta-analysis based on individual patient data", Clin. Pharmacol., (2002), 54:320-326.
Mammen et al., "PFA-100™ System: A New Method for Assessment of Platelet Dysfunction", Seminars in Thrombosis and Hemostasis, (1998), 24(2):195-202.
Mandell, "General Tolerability and Use of Nonsteroidal Anti-Inflammatory Drugs", The American Journal of Medicine, (1999), 107(6A):72S-76S.
McCabe et al., "Assessment of the antiplatelet effects of low to medium dose aspirin in the early and late phase after ischaemic stroke and TIA", Platelets, (2005), 16(5):269-280.
McGettigan et al., "Cardiovascular Risk and Inhibition of Cyclooxygenase. A Systematic Review of the Observational Studies of Selective and Nonselective Inhibitors of Cyclooxygenase 2", JAMA, (2006), 296(13):E1-E12.
Menasse et al, *Scand. J. Rheumatol. Suppl.* 22:5-16 (1978).
Maier et al., *Rheumatol. Rehabil.* Suppl. 2:11-21 (1979).

(56) References Cited

OTHER PUBLICATIONS

Mendham et al., "Comparison of diclofenac and tenoxicam for postoperative analgesia with and without fentanyl in children undergoing adenotonsillectomy or tonsillectomy", Paediatric Anaesthesia, (1996), 6:467-473.
Munsterhjelm et al., "Propacetamol augments inhibition of platelet function by diclofenac in volunteers", British Journal of Anaesthesia, (2003), 91(3):357-362.
Munsterhjelm et al., "Characterization of inhibition of platelet function by paracetamol and its interaction with diclofenac in vitro", Acta. Anaesthesiol. Scand., (2005), 49(6):840-846.
Niemi et al., "Comparison of the effect of intravenous ketoprofen, ketorolac and diclofenac on platelet function in volunteers", Acta. Anaesthesiol. Scand., (1997), 41:1353-1358.
Nekroshus et al., English Abstract of Russian Article, "Preparing the Inclusion Compounds Orthophen and Indomethcin with .beta.-Cyclodextrin and their Derivatographic Analysis", Farmatsiya Moscow, (1989), 38:29-34.
Nordbladh et al., "Analgesia in tonsillectomy: a double-blind study on pre and post-operative treatment with diclofenac", Clin. Otolaryngol., (1991), 16:554-558.
Ocana et al., "Potassium Channels and Pain: Present Realities and Future Opportunities", European Journal of Pharmacology, (2004), 500:203-219.
O'Hanlon et al., "A comparison of the effect of intramuscular diclofenac, ketorolac or piroxicam on post-operative pain following laparoscopy", European Journal of Anaesthesiology, (1996), 13:404-407.
Orienti et al., "Inclusion Complexes Between Non Steroidal Antiinflammatory Drugs and beta-Cyclodextrin", Dur. J. Pharm. Biopharm., (1991), 37(2):110-112.
Orienti et al., "Availability of NSAIDH beta-Cyclodextrin Inclusion Complexes", Arch. Pharm. (Weinheim), (1989), 322:207-211.
Otagiri et al., "Comparative Study on Inclusion Complexation of beta-Cyclodextrin and Tri-O-Methyl-beta-Cyclodextrin with Several Drugs in Aqueous Solution", Acta Pharm. Suec., (1984), 21:357-366.
Perttunen et al., "I.V. Diclofenac in post-thoracotomy pain", British Journal of Anaesthesia, (1992), 68:474-480.
Pilotto et al., "The risk of upper gastrointestinal bleeding in elderly users of aspirin and other non-steroidal anti-inflammatory drugs: the role of gastroprotective drugs", Aging Clin. Exp. Res., (2003), 15(6):494-499.
Pose-Vilarnovo et al., "Modulating Drug Release With Cyclodextrins in Hydroxypropyl methylcellulose gels and tablets", Journal of Controlled Release, (2004), 94:351-363.
Power et al., "Platelet function after intramuscular diclofenac", Anaesthesia, (1990), 45:910-919.
Reddy et al. "Beta Cyclodextrin Complexes of Celecoxib: Molecular Modeling, Characterization, and Dissolution Studies," AAPS Pharm. Sci., vol. 6, No. 1, 7, Mar. 5, 2005, pp. 1-9.
Reed et al., "Lysis of Human Red Blood Cells in the Presence of Various Cosolvents", Journal of Parenteral Science and Technology, (1985), 39(2):64-69.
Reer et al., "In Vitro Corneal Permeability of Diclofenac Sodium in Formulations Containing Cyclodextrins Compared to the Commercial Product Voltraren Ophtha", Journal of Pharmaceutical Sciences, (1994), 83(9):1345-1349.
Robinson et al., "Diclofenac and post-tonsillectomy haemorrhage", Clin. Otolatryngol., (1994), 19:344-345.
Robinson, "Correspondence: Diclofenac and post tonsillectomy haemorrhage", Clin. Otolatryngol., (1995), 20:483-484.
Romsing et al., "Diclofenac or acetaminophen for analgesia in paediatric tonsillectomy outpatients", Acta. Anaesthesiol. Scand., (2000), 44(3):291-295.
Rorarius et al., "Diclofenac versus indomethacin given as intravenous infusions: their effect on haemodynamics and bleeding time, and side-effects in healthy subjects", Annals of Clinical Research, (1985), 17:306-309.
Rorarius et al., "Effects of peri-operatively administered diclofenac and indomethacin on blood loss, bleeding time and plasma prostandoids in man", European Journal of Anaesthesiology, (1989), 6:335-342.
Saray et al., "Diclofenac and metamizol in postoperative analgesia in plastic surgery", Acta. Chirurgiae. Plasticae., (2001), 43(3):71-76.
Sia et al., "Combination of suppository diclofenac and intravenous morphine infusion in post-caesarean section pain relief—a step towards balanced analgesia?", Singapore Med. J., (1997), 38(2):68-70.
Schmidt et al., "Preoperative rectal diclofenac versus paracetamol for tonsillectomy: effects on pain and blood loss", Acta. Anaesthesiol. Scand., (2001), 45:48-52.
Seymour et al., *Eur. J. Clin. Pharmacol.* 56:447-452 (2000).
Sun et al., "Effects of Epidural Morphine and Intramuscular Diclofenac Combination in Postcesarean Analgesia: A Dose-Range Study", Anasth. Analg., (1993), 76:284-288.
Tai et al., "Comparison of controlled-release ketoprofen and diclofenac in the control of post-surgical dental pain", Journal of the Royal Society of Medicine, (1992), 85:16-18.
Thiagarajan et al. "Blood loss following tonsillectomy in children", Anaesthesia, (1993), 47:132-135.
Todd et al., *Drugs* 35(3): 244-85 (1988).
Uekama, "Cyclodextrin Inclusion Compounds: Effects on Stability and Bio-Pharmaceutical Properties", Elsevier Science Publishers B.V. (Biomedical Division), (1987), pp. 181-193.
Van Hecken et al., "Comparative Inhibitory Activity of Rofecoxib, Meloxicam, Diclofenac, Ibuprofen, and Naproxen on COX-2 versus COX-1 in Healthy Volunteers", J. Clin. Pharmacol., (2000), 40:1109-1120.
Yee et al., "Platelet hyperactivity generalizes to multiple forms of stimulation", Journal of Thrombosis and Haemostasis, (2006), 4:2043-2050.
U.S. Appl. No. 11/689,931, Oct. 14, 2011 Final Office Action.
U.S. Appl. No. 11/689,931, Aug. 4, 2011 Response to Non-Final Office Action.
U.S. Appl. No. 11/689,939, Aug. 4, 2011 Supplemental Amendment.
U.S. Appl. No. 11/689,939, Aug. 1, 2011 Amendment and Request for Continued Examination (RCE).
U.S. Appl. No. 11/689,931, Jan. 13, 2012 Amendment and Request for Continued Examination (RCE).
Cwiertni et al., "Stability of Dicolfenac Sodium in the Inclusion Complex with b-Cyclodextrin in the Solid State", J. Pharm. Pharmacol, 1999, vol. 51, pp. 1213-1218.
U.S. Appl. No. 11/689,939, Aug. 27, 2012 Non-Final Office Action.
U.S. Appl. No. 11/689,931, Aug. 28, 2012 Non-Final Office Action.
Japanese Office Action dated Aug. 29, 2012 from Japanese Application No. 2009-503166, (corresponding to U.S. Appl. Nos. 11/689,931 and 13/106,697).
Kore, et al., "Toxicology of Nonsteroidal Antiinflammatory Drugs", *Veterinary Clinics of North America, Small Animal Practice*, 20(2):419-430 (1990).
Gazarian, et al., "Safe use of NSAIDs in infants and children", *Medicine Today*, 7(11):7173 (2006).
Rekkas, et al., "Oral and intramuscular absorption of ibuprofen after administration of a freeze-dried ibuprofen 2-hp-beta-CD complex in dogs", *Proceedings of the International Symposium on Controlled Release of Bioactive Materials*, 24:557-558 (1997).
FDA Orange Book entry for ibuprofen intravenous solution, downloaded Aug. 20, 2012 from http://www.accessdata.fda.gov.
FDA Orange Book entry for ketorolac injectable solution, downloaded Aug. 20, 2012 from http://www.accessdata.fda.gov.
Routes of Administration Requiring Sterile Formulations, The Pharmaceutics and Compounding Laboratory, downloaded Aug. 20, 2012, from http://pharmlabs.unc.edu.
U.S. Appl. No. 13/153,283, Apr. 29, 2013 Response to Non-Final Office Action.
U.S. Appl. No. 11/689,931, Jul. 10, 2013 Notice of Allowance.
U.S. Appl. No. 13/153,283, Aug. 13, 2013 Final Office Action.
U.S. Appl. No. 14/051,021, filed Oct. 10, 2013.
U.S. Appl. No. 11/689,931, Oct. 9, 2013 Issue Fee payment.
U.S. Appl. No. 13/153,283, Nov. 29, 2012 Non-Final Office Action.

(56) References Cited

OTHER PUBLICATIONS

U.S. Appl. No. 11/689,931, Apr. 1, 2013 Amendment and Request for Continued Examination (RCE).
U.S. Appl. No. 11/689,931, Dec. 31, 2012 Final Office Action.
U.S. Appl. No. 11/689,931, Nov. 28, 2012 Response to Non-Final Office Action.
U.S. Appl. No. 10/999,155, Aug. 16, 2011 Notice of Abandonment.
U.S. Appl. No. 10/999,155, Dec. 6, 2010 Final Office Action.
U.S. Appl. No. 10/999,155, Nov. 4, 2010 Response to Non-Final Office Action.
U.S. Appl. No. 10/999,155, May 5, 2010 Non-Final Office Action.
U.S. Appl. No. 10/999,155, Mar. 18, 2010 Amendment and Request for Continued Examination (RCE).
U.S. Appl. No. 10/999,155, Aug. 18, 2009 Notice of Appeal.
U.S. Appl. No. 10/999,155, Feb. 20, 2009 Final Office Action.
U.S. Appl. No. 10/999,155, Sep. 15, 2008 Response to Non-Final Office Action.
U.S. Appl. No. 10/999,155, Jun. 11, 2008 Non-Final Office Action.
U.S. Appl. No. 10/999,155, Oct. 26, 2007 Response to Non-Final Office Action.
U.S. Appl. No. 10/999,155, Jul. 26, 2007 Non-Final Office Action.
Ammon, et al., "Diclofenac does not Interact with Codeine Metabolism in Vivo: A Study of Healthy Volunteers", *BMC Clinical Pharmacology*, 2(2):1-10 (2002).
Christensen, et al., "A Double-Blind Placebo-Controlled Comparison of a Novel Formulation of Intravenous Diclofenac and Ketorolac for Postoperative Third Molar Extraction Pain", *Anesth. Prog.*, 58:73-81 (2011).
Eddaoudi, et al., "Solubilities of the Cyclodextrins in the Presence of Transition Metal Salts", *Journal of Inclusion Phenomena and Molecular Recognition in Chemistry*, 26:133-151 (1996).
Eyjolfsson, "Diclofenac Sodium: Oxidative Degradation in Solution and Solid State", *Drug Development and Industrial Pharmacy*, 26(4):451-453 (2000).
Gaudiano, et al., "RP-HPLC Study of the Degradation of Diclofenac and Piroxican in the Presence of Hydroxyl Radicals", *Journal of Pharmaceutical and Biomedical Analysis*, 32:151-158 (2003).
Jansook, et al. "CD as Solubilizers: Effects of Excipients and Competing Drugs", *Int. J. Pharm*, 379(1):32-40 (2009).
Ledwidge, et al., "Effects of Surface Active Characteristics and Solid State Forms on the pH Solubility Profiles of Drug-Salt Systems", *Int. J. Pharm.*, 174(1-2):187-200 (1998).
Loftsson, et al. "Pharmaceutical Applications of Cyclodextrins: 1. Drug Solubilization and Stabilization", *Journal of Pharmaceutical Sciences*, 85(10):1017-1025 (1996).
Martin Del Valle, et al., "Cyclodextrins and Their Uses: A Review", *Process Biochemistry*, 39:1033-1046 (2004).
International Search Report and Written Opinion for PCT/IB2004/003918, dated Jun. 15, 2005.
International Preliminary Report on Patentability for PCT/IB2004/003918, dated Sep. 13, 2006.
International Search Report and Written Opinion for PCT/US2005/007354, dated Dec. 22, 2005.
International Preliminary Report on Patentability for PCT/US2005/007354, dated Sep. 13, 2006.
International Search Report and Written Opinion for PCT/US2012/047453, dated Oct. 4, 2012.
U.S. Appl. No. 13/153,283, Feb. 13, 2014 Non-Final Office Action.
Excerpts from Nursing Procedures: Intramuscular Injection Technique, AstraZeneca, 2000; pp. 243-247.

FORMULATIONS OF LOW DOSE DICLOFENAC AND BETA-CYCLODEXTRIN

CROSS-REFERENCE TO RELATED APPLICATIONS

This application is a continuation of application Ser. No. 11/689,931, filed Mar. 22, 2007 now U.S. Pat. No. 8,580,954, which claims priority under 35 U.S.C. §119, based on U.S. Provisional Application 60/786,486, filed Mar. 28, 2006. The disclosures of these applications are incorporated herein by reference in their entireties.

FIELD OF THE INVENTION

The present invention is directed to pharmaceutical compositions and methods of treating a subject in need of analgesia with pharmaceutical compositions which contain diclofenac and beta-cyclodextrin. Specifically, the compositions contain low doses of diclofenac, namely less than 10 mg.

BACKGROUND OF THE INVENTION

Diclofenac is a well-known non-steroidal anti-inflammatory drug ("NSAID") used in acute and chronic pain in both parenteral and oral dosage forms. Oral dosages range from 100-200 mg/day, while parenteral dosages range from 75-150 mg/day (1-2 mg/kg/day) by either infusion or intermittent (divided) doses. Toxicity of oral and parenteral forms are well known, with gastro-intestinal, hemorrhagic, renal, hepatic, cardiovascular and allergic (anaphylactic and severe dermal allergy) adverse events being most significant.

Parenteral use of diclofenac has been limited due to limited solubility, such that parenteral preparations have had to include non-polar solvents in order to achieve concentrations (75 mg/3 ml) which would allow intra-muscular (IM) administration of the desired dose. This solubility has limited the parenteral use to IM use and/or slow intravenous (IV) administration of diluted (100-500 ml diluent) product.

U.S. Pat. No. 5,679,660 and co-pending application Ser. No. 10/999,155, filed Nov. 30, 2004,published as US 2005/0238674 A1 on Oct. 27, 2005,both of which are incorporated by reference, disclose novel formulations of diclofenac with hydroxypropyl-beta-cyclodextrin, which allows a more concentrated preparation and thus rapid intravenous administration. The data show that the more concentrated the diclofenac/beta-cyclodextrin formulation, the faster onset of action over current products.

Other than ease of administration and more rapid onset of action, consequent on the improvements in the pharmaceutical formulation, no other advantages were observed. The present invention arises, in part, from the surprising discovery that formulating a non-steroidal anti-inflammatory drug with beta-cyclodextrin not only improves solubility and stability of the drug, it also increases efficacy.

SUMMARY OF THE INVENTION

The present invention relates to a pharmaceutical composition comprising a unit dose of a diclofenac compound effective to induce analgesia; and a beta-cyclodextrin compound, in which the dose of the diclofenac compound is less than 10 mg. This dose is less than any effective dose previously reported or even suggested for a formulation of a diclofenac and a beta-cyclodextrin compound. The diclofenac compound can be a diclofenac salt, e.g., diclofenac sodium, as exemplified infra. The beta-cyclodextrin compound can be 2-hydroxypropyl-beta-cyclodextrin, as exemplified infra.

The pharmaceutical composition may further comprise a stabilizer, such as monothioglycerol.

In specific embodiments, the pharmaceutical composition provides a dose of diclofenac of about 9.4 mg, less than about 5 mg, and even about 3.75 mg.

The invention further provides a method for treating a mammal in need of analgesia by administering a pharmaceutical composition of the invention, as set forth above. In a specific embodiment, the mammal is a human. In particular, the pharmaceutical composition can be administered intravenously.

The advantageous methods of the invention pertain to other formulations as well. Thus, the invention provides a method for treating a mammal in need of analgesia by administering a pharmaceutical composition comprising a dosage of a diclofenac compound effective to induce analgesia; and a beta-cyclodextrin compound, in which the dosage of the diclofenac compound is less than about 1.3 mg/kg per day. In particular embodiments, the dosage of diclofenac is less than 0.65 mg/kg per day, less than 0.33 mg/kg per day, or less than 0.165 mg/kg per day.

In another embodiment of the methods of treatment, the invention provides a method for treating a mammal in need of analgesia by administering a pharmaceutical composition comprising a dosage of a diclofenac compound effective to induce analgesia; and a beta-cyclodextrin compound, wherein the dosage of the diclofenac compound is less than a minimum approved dose for a particular route of administration. The dose of the diclofenac compound can have the same efficacy of pain relief as the minimum approved dose, or it can have from about 70% to about 100% or from about 40% to about 70% of the efficacy of pain relief as the minimum approved dose. In addition, the dose of the diclofenac compound can have the same duration of pain relief as the minimum approved dose, or it can have from about two-thirds to the same duration of pain relief, or from about one-third to about two-thirds of the duration of pain relief, as the minimum approved dose.

DETAILED DESCRIPTION OF THE INVENTION

The present invention provides formulations of a diclofenac compound with a beta-cyclodextrin compound. These formulations unexpectedly provide for significant efficacy and duration of pain relief at a lower dose than the current recommended doses of the diclofenac. More particularly, at a reduced dose and dosage, the formulation provides the same level of efficacy and the same duration of analgesia as at the minimum approved dose and dosage.

The invention is based, in part, on the results of a comparison of the efficacy of diclofenac solubilized with hydroxypropyl-beta-cyclodextrin to ketorolac and placebo for the treatment of moderate-to-severe post-surgical pain. The efficacy of diclofenac solubilized with hydroxypropyl-beta-cyclodextrin at several dose levels suggests a faster onset of action. Most notably, diclofenac formulated with hydroxypropyl-beta-cyclodextrin provides single-dose efficacy at about 50%, about 25%, about 12.5% and about 5% of the current recommended doses of diclofenac. This, in combination with the known human pharmacokinetic results for the formulation, supports reduced total daily doses of this NSAID with anticipated lower risk of toxicity by reducing the extent and duration of drug exposure. This is a novel finding and of clinical importance.

The minimum effective dose of diclofenac solubilized with hydroxypropyl-beta-cyclodextrin tested was 3.75 mg, demonstrating that diclofenac, if solubilized with hydroxypropyl-beta-cyclodextrin, may be administered at doses lower than those previously considered necessary for postoperative analgesia.

The term "diclofenac compound" refers to diclofenac or a pharmaceutically acceptable diclofenac salt. A pharmaceutically acceptable salt of diclofenac, can be an alkali metal salt, for example the sodium or the potassium salt, or the salt formed with an amine, e.g., a mono-, di- or tri-$C_1$-$C_4$ alkylamine, for example diethyl- or triethyl-amine, hydroxy-$C_2$-$C_4$ alkylamine, for example ethanolamine, or hydroxy-$C_2$-$C_4$ alkyl-$C_1$-$C_4$ alkylamine, for example dimethylethanolamine, or a quaternary ammonium salt, for example the tetramethylammonium salt or the choline salt of diclofenac (see, e.g., U.S. Pat. No. 5,389,681). Preferably the diclofenac salt is diclofenac sodium.

Suitable formulations of the present invention for parenteral administration include cyclodextrin inclusion complexes. One or more modified or unmodified cyclodextrins can be employed to stabilize and increase the water solubility and efficacy of compounds of the present invention. Useful cyclodextrins for this purpose include beta-cyclodextrins.

The term "beta-cyclodextrin" as used herein refers to cyclic alpha-1,4-linked oligosaccharides of a D-glucopyranose containing a relatively hydrophobic central cavity and hydrophilic outer surface. Particular efficacy has been observed in the present invention utilizing hydroxypropyl-beta-cyclodextrin, however, other substituted and unsubstituted beta-cyclodextrins can also be used in the practice of the invention. Additional examples of cyclodextrins that may be utilized are disclosed in U.S. Pat. Nos. 4,727,064, 4,764,604, 5,024,998, 6,407,079, 6,828,299, 6,869,939 and Jambhekar et al., 2004 Int. J Pharm. 2004, 270(1-2) 149-66.The formulations may be prepared as described in U.S. Pat. Nos. 5,679,660 and 5,674,854.

The "pharmaceutical compositions" for use in accordance with the present invention can be formulated in any conventional manner using one or more pharmaceutically acceptable carriers or excipients. A "pharmaceutically acceptable" carrier or excipient, as used herein, the term "pharmaceutically acceptable" means approved by a regulatory agency of the Federal or a state government or listed in the U.S. Pharmacopoeia or other generally recognized pharmacopoeia for use in mammals, and more particularly in humans.

Pharmaceutical compositions include solid dosage forms, e.g., for perioral, transnasal (powder), or rectal (suppository) administration; and liquid dosage forms, e.g., for parenteral administration (injection), transnasal (spray), or perioral administration. In a specific embodiment, the pharmaceutical compositions of the present invention are liquid compositions formulated for intravenous or intramuscular administration, and particularly intravenous administration.

As used herein, the term "stabilizer" refers to a compound optionally used in the pharmaceutical compositions of the present invention in order to avoid the need for sulphite salts and increase storage life. Optimal stabilizers include antioxidants, specifically monothioglycerol and those described in U.S. Patent Publication 2005/0238674.

The term "dosage" is intended to encompass a formulation expressed in terms of mg/kg/day. The dosage is the amount of an ingredient administered in accordance with a particular dosage regimen. A "dose" is an amount of an agent administered to a subject in a unit volume or mass, e.g., an absolute unit dose expressed in mg of the agent. The dose depends on the concentration of the agent in the formulation, e.g., in moles per liter (M), mass per volume (m/v), or mass per mass (m/m). The two terms are closely related, as a particular dosage results from the regimen of administration of a dose or doses of the formulation. The particular meaning in any case will be apparent from context.

The term "mammal" is intended to include, any warm-blooded vertebrate having the skin more or less covered with hair. Most preferably, the mammal is a human subject, but the mammal can also be a non-human animal. Thus, the invention is useful in veterinary medicine as well, e.g., for treating pain in a domestic pet, such as a canine or feline, a farm animal, a work animal, or an animal in a circus or zoological garden. The invention has particular value in treating pain in a horse, particularly in sport, such as thoroughbred and other race horses, rodeo horses, circus horses, and dressage horses. A particular advantage of the invention is that, by increasing the efficacy of a dosage of diclofenac, it is possible to administer a therapeutic dosage that is below a maximum allowed dose permitted by the particular regulatory authorities of the sport.

The term "minimum approved dose" refers to the minimum dosage that has received full regulatory approval by the appropriate United States or foreign regulatory authority as safe and effective for human or veterinary use.

The term "therapeutically effective" as applied to dose or amount refers to that quantity of a compound or pharmaceutical composition that is sufficient to result in a desired activity upon administration to a mammal in need thereof. As used herein with respect to the pharmaceutical compositions comprising an antifungal, the term "therapeutically effective amount/dose" refers to the amount/dose of a compound or pharmaceutical composition that is sufficient to produce an effective response upon administration to a mammal.

The term "amount" as used herein refers to quantity or to concentration as appropriate to the context. In the present invention, the effective amount of a compound refers to an amount sufficient to treat a patient/subject in need of analgesia. The effective amount of a drug that constitutes a therapeutically effective amount varies according to factors such as the potency of the particular drug, the route of administration of the formulation, and the mechanical system used to administer the formulation. A therapeutically effective amount of a particular drug can be selected by those of ordinary skill in the art with due consideration of such factors.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

As used herein, the term "treat" is used herein to mean to relieve or alleviate at least one symptom of a disease in a subject. Within the meaning of the present invention, the term "treat" also denotes to arrest, delay the onset (i.e., the period prior to clinical manifestation of a disease) and/or reduce the risk of developing or worsening a disease.

Methods of Treatment

As noted above, the novel dosage formulations of the invention are suitable for administering diclofenac to treat pain, i.e., for analgesia. Various embodiments of the invention provide for administration of unit doses to achieve a total dosage for the desired effect. The examples demonstrate efficacy of a 3.75 mg dose of diclofenac, which is about 5% of the minimum approved dose (and about 5% or about 2.5% of the approved daily dosage). However, this dose provides about 40% of the pain relief and one-third of the duration as the minimum approved dose. Better results can be achieved by selecting a dosage regimen with this dose of diclofenac, e.g., increasing the frequency of administration, to achieve a level and duration of pain relief acceptable for the patient. Higher dose formulations likewise could provide such relief. Such higher dose formulations are nevertheless lower than any approved formulation, and the dosage regimen results in administration of less diclofenac than the current approved minimum dosage regimen.

A significant advantage of the invention results from the ability to achieve efficacy with lower doses and overall daily dosing of diclofenac. Consequently, it is possible to reduce the dosage, and thus reduce toxicity.

In specific embodiments, the unit dose (i.e., the amount of active drug administered at one time to a patient) is no more than about 75%, no more than about 50%, no more than about 25%, no more than about 12.5%, and no more than about 5%, of the approved minimum dose. Doses that are about or greater than about 50% of the approved minimum dose can show the same level and duration of pain relieve as the minimum effective dose. Furthermore, by increasing the frequency of administration of a lower dose formulation, the patient can achieve the same levels of efficacy and duration of pain relief as with the approved doses, with decreased toxicity.

In another embodiment, then, the invention provides for titrating the dose reduction of diclofenac and beta-cyclodextrin by decreasing the unit dose to achieve an analgesic effect that is sufficient, even at a reduced level, for the patient's needs, which can be met by increasing the dosing frequency to achieve an effective daily dosage that is still lower than the minimum approved dose. The term "effect" means that there is a statistically significant difference in a response in patients taking the formulation containing the diclofenac relative to patients taking a placebo.

The formulations of the invention can be administered via any route, including parenteral, perioral, transnasal, and rectal. Particular parenteral routes of administration include intravenous and intramuscular injection.

The formulations of the invention are suitable for treating pain by administration either or both prophylactically and after onset of the pain. Thus, as used herein, the term "treat" (in any of its grammatical forms) means to reduce pain through administration of a formulation of the invention prior to or after the onset of pain, or both. In particular, the formulations are suitable in the treatment of acute painful conditions in humans and animals such as headache, including migraine, trauma, dysmenorrhoea, renal or biliary colic, post-operative pain, gout, arthritis, cancer related pain, musculoskeletal pain, lower back pain, fibromyalgia, and pain of infectious origin. Indeed, the low dosage of diclofenac will have little or no anti-inflammatory activity, so in the treatment of pain of infectious origin it will have little effect on any immune response to the infectious organism while achieving analgesia. In a specific embodiment, exemplified below, the formulation is effective to treat post-surgical dental pain resulting from surgical extraction of one or more third molars. In addition, although not intending to be bound by any particular mechanism of action, the formulation of the invention may be used prophylactically to prevent the formation of prostaglandins during and after surgery, with subsequent reduction in immediate post-operative pain. Further, the formulation of the invention may be used to modulate nuclear transcription factors, such as NF-κB, or to modulate ion channel activity, for example as described in Ocana, Maria et al., *Potassium Channels and Pain: Present Realities and Future Opportunities*, 500 Eur. J. Pharm. 203 (2004).

EXAMPLES

The present invention will be better understood by reference to the following Examples, which are provided as exemplary of the invention, and not by way of limitation.

Example 1

Analysis of Pain Relief Afforded to Patients Based on Administered Dose

A 336-patient, seven treatment arm, randomized, double-blind, single-dose, and placebo- and comparator-controlled, parallel-group study was conducted. Patients were randomly assigned to receive a single dose of either diclofenac sodium solubilized with hydroxypropyl-beta-cyclodextrin (hereinafter "DIC"), ketorolac tromethamine, or placebo.

Bolus IV injectable 2 ml solutions were prepared by solubilizing diclofenac sodium with hydroxypropyl-beta-cyclodextrin. The formulation strengths were as follows:
Formulation: Diclofenac sodium solubilized with hydroxypropyl-β-cyclodextrin
Strengths: 75 mg, 37.5 mg, 18.75 mg, 9.4 mg and 3.75 mg
Dosage: Bolus IV injection (no less than 15 sec)
Batch Number: 063004 (PPS04010)
Manufacturer: Manufactured for Javelin by Precision Pharma
Storage Conditions: Room temperature
Active control/comparator:
Formulation: Ketorolac Tromethamine
Strength: 30 mg
Dosage: Bolus IV injection (no less than 15 sec)
Batch Number: 21-430-DK
Manufacturer: Abbott Labs
Storage Conditions: Room temperature
Pain was assessed by each patient at Baseline (0 hour: Visual Analog Scale (VAS) and categorical pain intensity only), at 5, 15, 30 and 45 minutes, and at 1, 1.5, 2, 3, 4, 5, 6, 7, 8, 10, 12 and 24 hours after administration of study medication and immediately prior to the first dose of rescue medication. At each post-dose time period, levels of pain intensity (categorical and VAS) and pain relief (categorical and VAS)

was assessed by each patient. Patients were also provided with 2 stopwatches to measure perceptible and meaningful pain relief.

The presence of a dose-response was tested with a step-down testing procedure. Total pain relief (TOTPAR), peak pain relief, pain intensity difference (SPID), summed peak reduction in pain intensity difference (SPRID), and patient global evaluation was analyzed with analysis of variance (ANOVA) with treatment, center, and baseline categorical pain intensity as factors. The possibility of interactions was investigated. Comparisons of the DIC groups with the placebo and Ketorolac groups were performed with Dunnett's test. The presence of a linear dose response for the ordered DIC dose levels was tested with orthogonal contrasts for TOTPAR, SPID and SPRID. Tests of individual DIC dose levels versus placebo for TOTPAR, SPID, and SPRID were conducted with the Tukey, Ciminera, and Heyse step-down testing procedure. The mean, standard deviation, and sample size were presented for each treatment group. Significant p-values (those less than or equal to 0.05) were presented for each step of the procedure. Non-significant p-values were represented with three dashes. Time to onset of perceptible relief and time to onset of meaningful relief was analyzed with survival analysis techniques. These variables were summarized with number of observations, mean, standard deviation, median, and range. Log-rank tests were used to compare treatments with respect to survival distributions. The median time to event for each treatment group was estimated with the Kaplan-Meier product limit estimator. A 95% confidence interval for each estimated median time to event was calculated.

The results of the study were strongly positive, novel and could not have been anticipated from prior experience with diclofenac. The doses had been chosen based on the currently recommended minimally effective doses of 1 mg/kg (50 mg immediate-release or 100 mg sustained-release orally or 75 mg intramuscularly or intravenously). Based on these doses the test conditions were a full dose (75 mg), half dose (37.5) mg, a possibly effective dose (18.75 mg) and two placebo doses (9.75 & 3.4 mg). The findings were as follows:

TABLE 1

TOTPAR (Sum of Pain Relief VAS 0-100 mm ratings 0-6 hours)

| Treatment Group | Result | % Maximum Effect |
| --- | --- | --- |
| Placebo | 62.8 (SEM 9) | 17% |
| DIC 3.75 mg | 134.1 (SEM 8) | 38% |
| DIC 9.4 mg | 237.6 (SEM 15) | 68% |
| DIC 18.75 mg | 284.4 (SEM 21) | 82% |
| DIC 37.5 mg | 348.2 (SEM 30) | 100% |
| DIC 75 mg | 346.3 (SEM 27) | 100% |
| ketorolac | 400.3 (SEM 36) | 100% |

Figure 1:
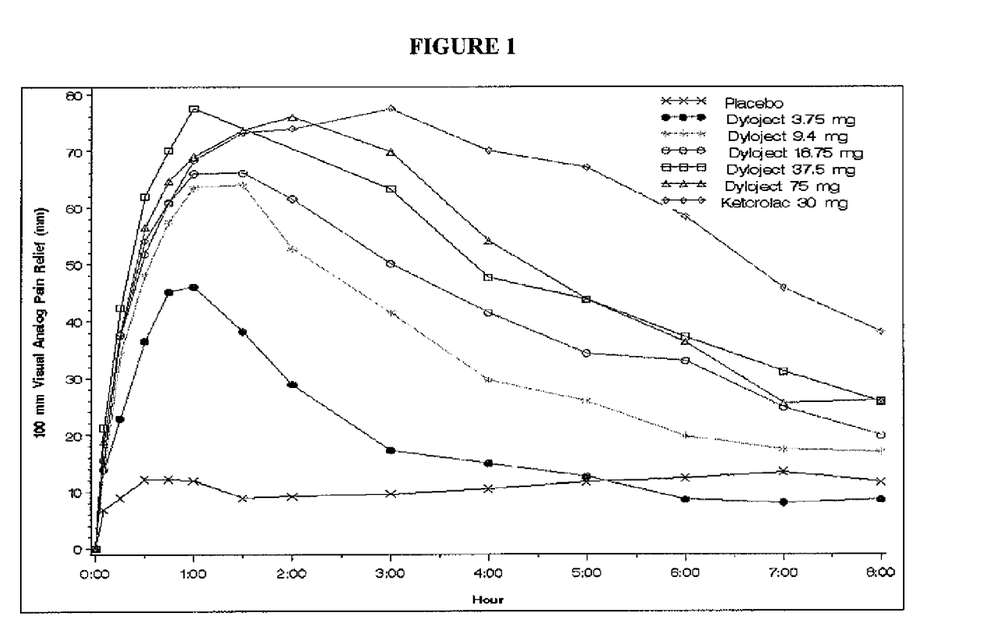
FIG. 1 contains a graphical representation of the 100 mm visual analog pain relief (mm) afforded to patients over time (hours) based on the formulation strengths administered. The tested formulations include placebo, 3.75 mg Dyloject, 9.4 mg Dyloject, 18.75 mg Dyloject; 37.5 mg Dyloject, 75 mg Dyloject, and 30 mg Ketorolac.

See FIG. 1 for the corresponding graphical representation of the pain relief afforded to patients based on the formulation strengths administered.

Example 2

Analysis of Efficacy & Duration of Pain Relief at Lower Doses of Diclofenac

Figure 2:
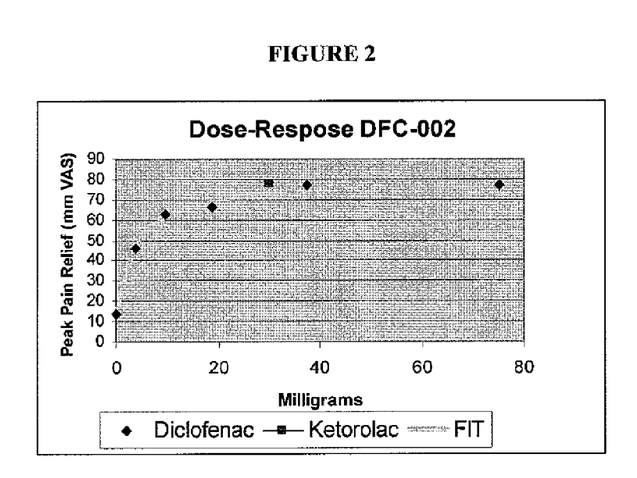
FIG. 2 illustrates the dose-response curve for peak analgesia observed (mm VAS) over mg of formulation. Both diclofenac and ketorolac formulations were tested.

To explore this further, the dose-duration relationship in the same study was examined using the median time to remedication in the single-dose phase. Utilizing the results of study in Example 1, the efficacy and duration of pain relief were thoroughly analyzed. The lowest IV dose of DIC (3.75 mg) had 38% of the effect of the maximal dose, and the next lowest dose (9.4 mg) had 68% of the maximal possible effect, despite being 5% and 12% respectively of the current recommended minimally effective dose (1 mg/kg). FIG. 2 contains a graphical illustration of the dose-response for peak analgesia observed in the study.

Figure 3:
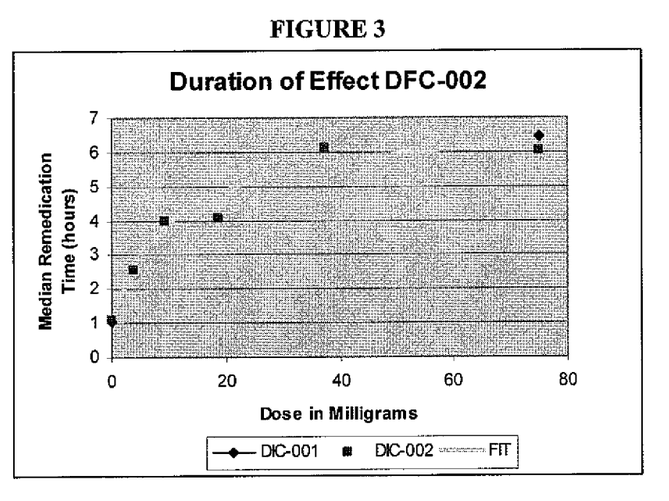
FIG. 3 illustrates the dose-duration relationship examined using the median time to re-medication (hours) in the single dose phase. Two formulations of diclofenac were studied.
Figure 4:
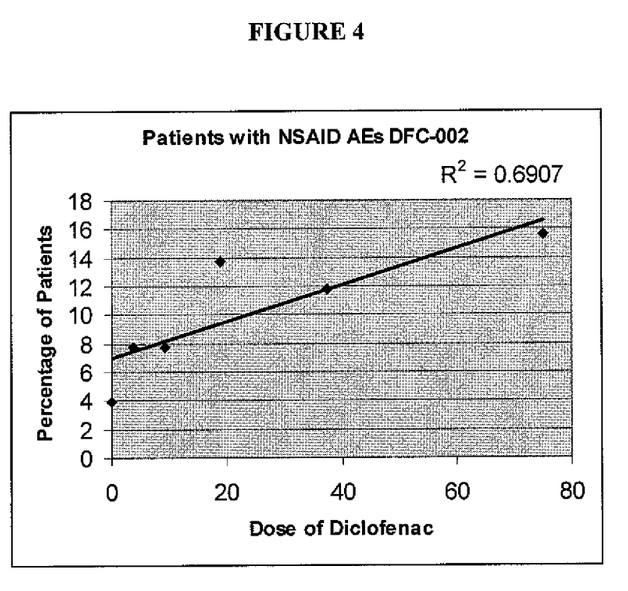
FIG. 4 illustrates the percentage of patients with NSAID Adverse Events by dose of diclofenac (mg).

FIG. 3 depicts the dose-duration relationship examined using the median time to remedication in the single dose phase. The peak analgesic response was about 80% pain relief, with a 50% response at a dose of 4-8 milligrams of Diclofenac in relation to dental pain. Similar peak analgesic response was seen for 30 milligrams of ketorolac. Given the shape of the dose response curve, it is clear that lower doses of the DIC formulation achieved the same results as the current established dose of diclofenac of 75 milligrams.

The findings show a 6 hour duration of effect for all doses above about 20 milligrams (18 milligrams).

For most drugs the findings of significant activity at doses far below the recommended doses would be of little significance due to large therapeutic indices (wide ranges between the effective and toxic doses). The opposite is true for parenteral NSAIDs; it has been well established in the prior art that increasing the dose of these drugs rapidly diminishes their utility due to increasing risk of toxicity.

Thus the finding that with the new formulation of diclofenac that 5%-12% of the usual dose can provide 38-68% of the desired therapeutic effect is remarkable and unanticipated. This leads to the possibility that the high early blood levels possible with the new formulation allow lower total daily doses resulting in less risk of toxicity.

This finding demonstrates efficacy with a lower daily dose (25-75 mg/day) than current dosing of diclofenac (75-200 mg/day), and anticipates better dosing paradigms (less than Q 12 hours) offering the expectation of lesser toxicity. Proof of lesser toxicity from available data from this study is suggestive, based on the known relationship of dose and toxicity.

The novel diclofenac formulation allowed by hydroxypropyl-β-cyclodextrin has been shown to provide proof of single-dose efficacy at 50%, 25%, 12.5% and 5% of the current recommended doses of diclofenac. This in combination with the known human pharmacokinetic results for the formulation supports reduced total daily doses of this NSAID with anticipated lower risk of toxicity by reducing the extent and duration of drug exposure.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Patents, patent applications publications product descriptions, and protocols are cited throughout this application the disclosures of which are incorporated herein by reference in their entireties for all purposes.

What is claimed is:
1. A method of providing analgesia to a subject in need thereof, which method comprises parenterally administering to the subject a pharmaceutical composition, wherein the composition comprises:
(a) from about 18.75 mg to about 37.5 mg of a diclofenac compound; and
(b) a beta-cyclodextrin compound;
wherein the dosage of the diclofenac compound is less than about 1.3 mg/kg per day; and wherein the method achieves at least about 82% of maximum observable total pain relief assessed by a Visual Analog Scale.

2. The method of claim 1, wherein the diclofenac compound is diclofenac sodium.

3. The method of claim 1, wherein the pharmaceutical composition is administered intravenously.

4. The method of claim 1, wherein the dose of the diclofenac compound is 18.75 mg (+/−20%).

5. The method of claim 1, wherein the dose diclofenac compound is 37.5 mg (+/−20%).

* * * * *